United States Patent
Zerkowski et al.

(10) Patent No.: US 7,718,782 B2
(45) Date of Patent: May 18, 2010

(54) CHARGED SOPHOROLIPIDS AND SOPHOROLIPID CONTAINING COMPOUNDS

(75) Inventors: Jonathan Zerkowski, Strafford, PA (US); Daniel Solaiman, Dresher, PA (US); Richard D. Ashby, Glenside, PA (US); Thomas A. Foglia, Lafayette Hill, PA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 550 days.

(21) Appl. No.: 11/484,214

(22) Filed: Jul. 11, 2006

(65) Prior Publication Data
US 2007/0027106 A1    Feb. 1, 2007

Related U.S. Application Data

(60) Provisional application No. 60/702,469, filed on Jul. 26, 2005.

(51) Int. Cl.
C07H 17/02 (2006.01)
A61K 31/70 (2006.01)
A01N 43/04 (2006.01)
(52) U.S. Cl. .......... 536/17.9; 536/17.4; 514/25
(58) Field of Classification Search ............... None
See application file for complete search history.

(56) References Cited

OTHER PUBLICATIONS

Asmer, Hans-Joachim et al., "Microbial Production, Structure Elucidation and BioConversion Of Sophorose Lipids," *JAOCS*, Sep. 1998, vol. 65, No. 9, pp. 1460-1466.
Cavalero, David A. et al., "The Effect of Medium Composition on the Structure and Physical State of Sorphorolipids Produced by *Candida bombicola* ATCC 22214," *Journal of Biotechnology*, 2003, vol. 103, pp. 31-41.
Solaiman, Daniel K.Y.et al., "Production of Sophorolipids by *Candida bombicola* grown on Soy Molasses as Substrate,"*Biotechnology Letters*, 2004, vol. 26, pp. 1241-1245.
Chevalier Yves, "New Surfactants: New Chemical Functions and Molecular Architectures," *Current Opinion in Colloid & Interface Science*, 2002, vol. 7, pp. 3-11.
Zhang, Lei et al., "Synthesis and Interfacial Properties of Sophorolipid Derivatives," *Colloids and Surfaces A*,2004,vol. 240, pp. 75-82.
Singh, Sanjay K. et al., "Regioselective Enzyme-Catalyzed Synthesis of Sophorolipid Esters, Amides, and Multifunctional Monomers ," *JOC Article*, 2003, vol. 68, pp. 5466-5477.
Lang, Siegmund et al., "Production of Native and Modified Sophorose Lipids," *Chemisty Today*, Oct. 2000.
Carr, Jason A. et al., "Enzyme-Catalyzed Regioselective Transesterification of Peraxylated Sophorolipids," *Tetrahedron*, 2003, vol. 59, pp. 7713-7724.
Bisht, Kirpal S. et al., "Glycolipids from *Candida bombicola*: Polymerization of a 6-O-Acryloyl Sophorolipid Dervative," *Macromolecules*, 2000, vol. 33, pp. 6208-6210.
Bisht, Kirpal S. et al., "Enzyme-Medicated Regioselective Acylationsof Sophorolipids," *Journal of Organic Chemistry*, 1999, vol. 64, pp. 780-789.

Primary Examiner—Shaojia Anna Jiang
Assistant Examiner—Layla Bland
(74) Attorney, Agent, or Firm—John D. Fado; G. Byron Stover

(57) ABSTRACT

A sophorolid produced by a method involving reacting a compound of formula I

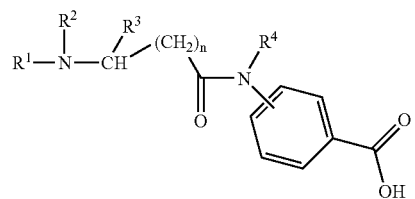

I with a compound of formula II

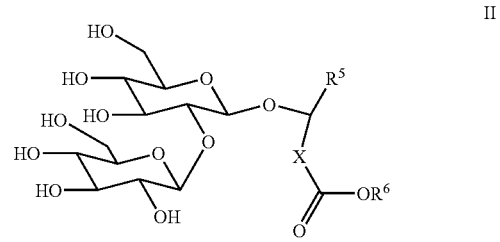

II wherein
$R^1$ and $R^2$ are H, $C_1$-$C_{18}$ alkyl, $C_3$-$C_{18}$ alkenyl, $C_3$-$C_{10}$ cycloalkyl, phenyl, or $C_1$ through $C_{18}$ acyl or alkoxycarbonyl,
$R^1$ and $R^2$ are not both acyl,
$R^3$ is H, $CH_3$, $CH_2$-phenyl, $CH_2$—$C_6H_4$—OH, $CH_2CO_2H$, $CH_2CH_2CO_2H$, $CH(CH_3)_2$, $CH_2CH(CH_3)_2$, $CH(CH_3)$ $CH_2CH_3$, $CH_2OH$, $CH(CH_3)OH$, $CH_2CH_2CH_2CH_2NH_2$, $CH_2CH_2CONH_2$, $CH_2CONH_2$, $CH_2$—$C_3N_2H_3$(histidine), $CH_2CH_2CH_2NHC(NH)NH_2$, $CH_2CH_2SCH_3$,
$R^2$ and $R^3$ may be joined in a ring,
$R^4$ is H, $C_1$-$C_{18}$ alkyl, $C_3$-$C_{18}$ alkenyl, $C_3$-$C_{10}$ cycloalkyl, or phenyl,
n is 0-6,
$R^5$ and $R^6$ are H, $C_1$-$C_{18}$ alkyl, $C_3$-$C_{18}$ alkenyl, $C_3$-$C_{10}$ cycloalkyl, or phenyl, and
X is $C_1$-$C_{18}$ alkyl or $C_1$-$C_{18}$ alkenyl;
optionally followed by acidolytic (treating with an acid) or hydrogenolytic deprotection (treating with a hydrogenolysis catalyst) which removes one of the groups $R^1$ or $R^2$ and replaces it with hydrogen. Also a sophorolipid containing composition containing a carrier and at least one sophorolipid described above.

13 Claims, 2 Drawing Sheets

CHARGED SOPHOROLIPIDS AND SOPHOROLIPID CONTAINING COMPOUNDS

REFERENCE TO RELATED APPLICATION

This application claims the benefit of U.S. Provisional Application No. 60/702,469, filed 26 Jul. 2005, which is incorporated herein by reference in its entirety.

BACKGROUND OF THE INVENTION

The present invention relates to a sophorolid, wherein the sophorolid is produced by a method involving reacting a compound of formula I

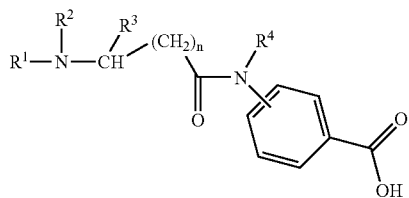

with a compound of formula II

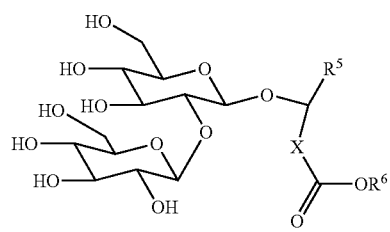

wherein $R^1$ and $R^2$ are H, $C_1$-$C_{18}$ alkyl, $C_3$-$C_{18}$ alkenyl, $C_3$-$C_{10}$ cycloalkyl, phenyl, or $C_1$ through $C_{18}$ acyl or alkoxycarbonyl, $R^1$ and $R^2$ are not both acyl, $R^3$ is H, $CH_3$, $CH_2$-phenyl, $CH_2$—$C_6H_4$—OH, $CH_2CO_2H$, $CH_2CH_2CO_2H$, $CH(CH_3)_2$, $CH_2CH(CH_3)_2$, $CH(CH_3)CH_2CH_3$, $CH_2OH$, $CH(CH_3)OH$, $CH_2CH_2CH_2CH_2NH_2$, $CH_2CH_2CONH_2$, $CH_2CONH_2$, $CH_2$—$C_3N_2H_3$(histidine), $CH_2CH_2CH_2NHC(NH)NH_2$, $CH_2CH_2SCH_3$, $R^2$ and $R^3$ may be joined in a ring, $R^4$ is H, $C_1$-$C_{18}$ alkyl, $C_3$-$C_{18}$ alkenyl, $C_3$-$C_{10}$ cycloalkyl, or phenyl, n is 0-6, $R^5$ and $R^6$ are H, $C_1$-$C_{18}$ alkyl, $C_3$-$C_{18}$ alkenyl, $C_3$-$C_{10}$ cycloalkyl, or phenyl, and X is $C_1$-$C_{18}$ alkyl or $C_1$-$C_{18}$ alkenyl;

optionally followed by acidolytic deprotection (treating with an acid) or hydrogenolytic deprotection (treating with a hydrogenolysis catalyst) which removes one of the groups $R^1$ or $R^2$ and replaces it with hydrogen. In addition, the present invention relates to a sophorolipid containing composition containing a carrier and at least one sophorolipid described above.

Sophorolipids (SL) are hydroxy fatty acid glycosides that can be produced in good yields (e.g., around 100 g/L) by microbial fermentation of a wide variety of feedstocks (Asmer, H.-J., et al., J. Am. Oil. Chem. Soc., 65: 1460-1466 (1988); Cavalero, D. A., and D. G. Cooper, J. Biotech., 103: 31-41 (2003)). Agricultural byproducts such as tallow or soy molasses can be converted into these interesting glycolipids (Solaiman, D. K. Y., et al., Biotech. Lett., 26: 1241-1245 (2004)). The material as produced consists of a number of closely related variants, including a lactone (closed chain) and an open-chain form, each of which may bear up to two acetyl groups. Furthermore, depending on the feedstock, the predominantly C-18 lipid chain can be predominantly a stearic or oleic acid derivative or a mixture. The crude material possesses surfactant activity and might be used as an eco-friendly detergent. Its structural multiplicity, however, complicates attempts to correlate molecular shape with surfactant behavior. We have found ways in which the fundamental sophorolipid skeleton can be chemically modified to increase its utility as a surfactant, in particular by increasing the water-solubility of SLs with charged head groups.

SUMMARY OF THE INVENTION

In accordance with the present invention there is provided a sophorolipid wherein the sophorolid is produced by a method involving reacting a compound of formula I

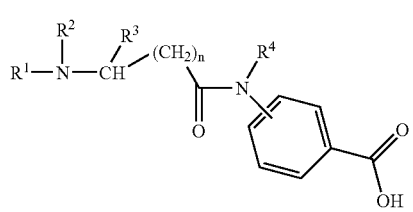

with a compound of formula II

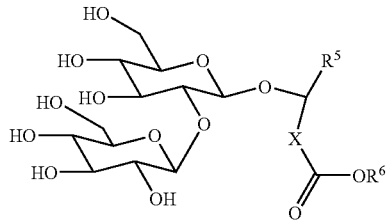

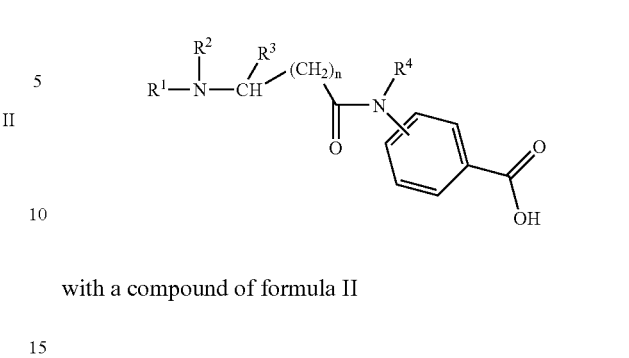

with a compound of formula II

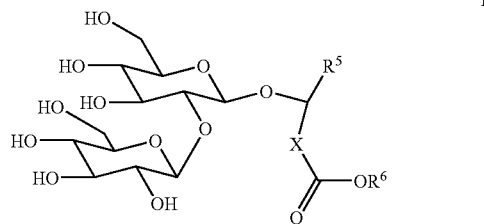

wherein $R^1$ and $R^2$ are H, $C_1$-$C_{18}$ alkyl, $C_3$-$C_{18}$ alkenyl, $C_3$-$C_{10}$ cycloalkyl, phenyl, or $C_1$ through $C_{18}$ acyl or alkoxycarbonyl, $R^1$ and $R^2$ are not both acyl, $R^3$ is H, $CH_3$, $CH_2$-phenyl, $CH_2$—$C_6H_4$—OH, $CH_2CO_2H$, $CH_2CH_2CO_2H$, $CH(CH_3)_2$, $CH_2CH(CH_3)_2$, $CH(CH_3)CH_2CH_3$, $CH_2OH$, $CH(CH_3)OH$, $CH_2CH_2CH_2CH_2NH_2$, $CH_2CH_2CONH_2$, $CH_2CONH_2$, $CH_2$—$C_3N_2H_3$(histidine), $CH_2CH_2CH_2NHC(NH)NH_2$, $CH_2CH_2SCH_3$, $R^2$ and $R^3$ may be joined in a ring, $R^4$ is H, $C_1$-$C_{18}$ alkyl, $C_3$-$C_{18}$ alkenyl, $C_3$-$C_{10}$ cycloalkyl, or phenyl, n is 0-6, $R^5$ and $R^6$ are H, $C_1$-$C_{18}$ alkyl, $C_3$-$C_{18}$ alkenyl, $C_3$-$C_{10}$ cycloalkyl, or phenyl, and X is $C_1$-$C_{18}$ alkyl or $C_1$-$C_{18}$ alkenyl;

optionally followed by acidolytic deprotection (treating with an acid) or hydrogenolytic deprotection (treating with a hydrogenolysis catalyst) which removes one of the groups $R^1$ or $R^2$ and replaces it with hydrogen. Also in accordance with the present invention, there is provided a sophorolipid containing composition containing a carrier and at least one sophorolipid described above.

DETAILED DESCRIPTION OF THE INVENTION

Figure 1:
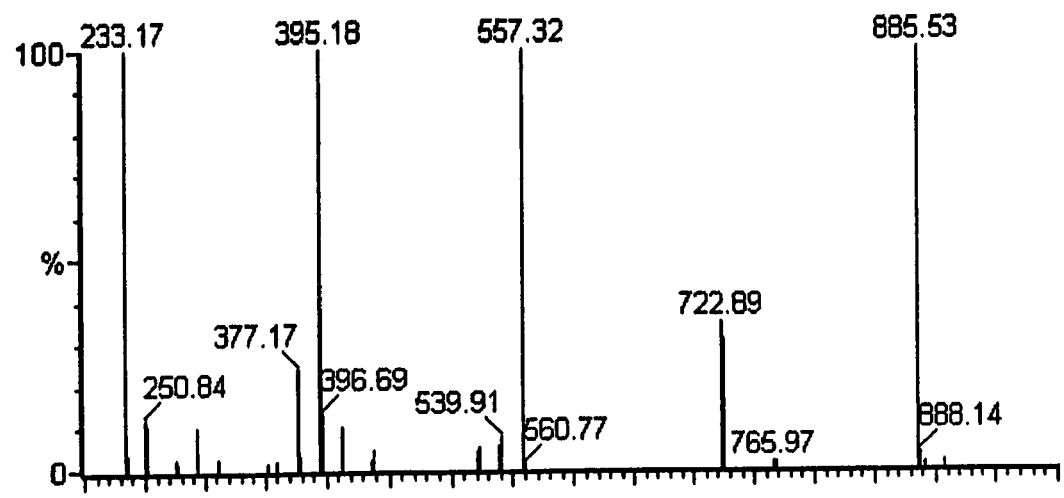
FIG. 1 shows the mass spectra of the two major isomers of compound IVb (described below). The peak at 722 in the top spectrum indicated loss of one glucose unit from the sophorose headgroup. The peak at 557 occurred from loss of the ethyl hydroxystearate side chain.
Figure 1:
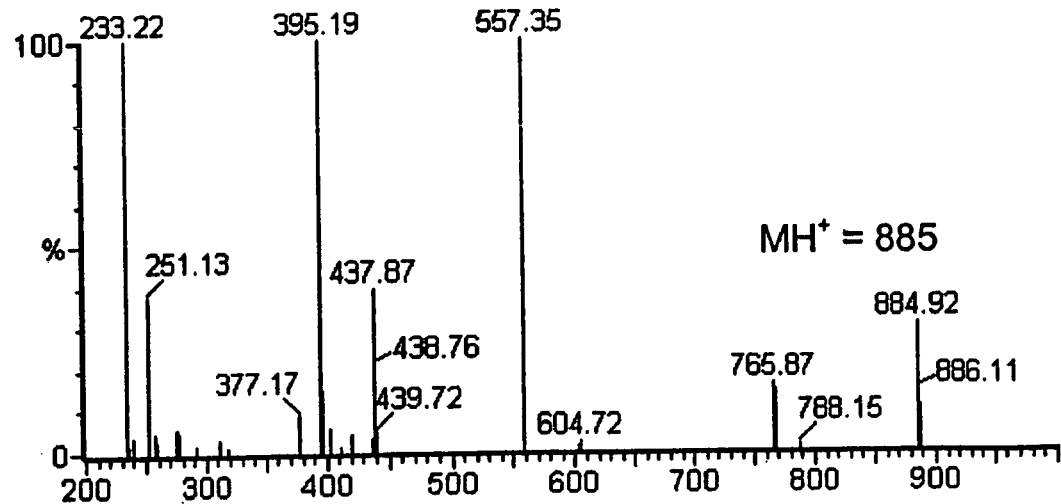

The present invention relates to a sophorolid produced by a method involving reacting a compound of formula I and condensation reagents (e.g., 1-[3-(dimethylamino)propyl]-3-ethylcarbodiimide hydrochloride, hydroxybenzotriazole, 4-dimethylaminopyridine), wherein $R^1$ and $R^2$ are H, $C_1$-$C_{18}$ alkyl, $C_3$-$C_{18}$ alkenyl, $C_3$-$C_{10}$ cycloalkyl, phenyl, or $C_1$ through $C_{18}$ acyl or alkoxycarbonyl, $R^1$ and $R^2$ are not both acyl, $R^3$ is H, $CH_3$, $CH_2$-phenyl, $CH_2$—$C_6H_4$—OH, $CH_2CO_2H$, $CH_2CH_2CO_2H$, $CH(CH_3)_2$, $CH_2CH(CH_3)_2$, $CH(CH_3)CH_2CH_3$, $CH_2OH$, $CH(CH_3)OH$, $CH_2CH_2CH_2CH_2NH_2$, $CH_2CH_2CONH_2$, $CH_2CONH_2$, $CH_2$—$C_3N_2H_3$(histidine), $CH_2CH_2CH_2NHC(NH)NH_2$, $CH_2CH_2SCH_3$, $R^2$ and $R^3$ may be joined in a ring (cyclized), $R^4$ is H, $C_1$-$C_{18}$ alkyl, $C_3$-$C_{18}$ alkenyl, $C_3$-$C_{10}$ cycloalkyl, or phenyl, n is 0-6, $R^5$ and $R^6$ are H, $C_1$-$C_{18}$ alkyl, $C_3$-$C_{18}$ alkenyl, $C_3$-$C_{10}$ cycloalkyl, or phenyl, and X is $C_1$-$C_{18}$ alkyl or $C_1$-$C_{18}$ alkenyl;

optionally followed by acidolytic deprotection (treating with an acid) or hydrogenolytic deprotection (treating with a hydrogenolysis catalyst) which removes one of the groups $R^1$ or $R^2$ and replaces it with hydrogen. The present invention also relates to a sophorolipid containing composition containing a carrier (e.g., water, methanol, ethanol) and at least one sophorolipid described above.

Preferably $R^1$ and $R^2$ are H, methyl, or $C_1$ through $C_{18}$ acyl or alkoxycarbonyl, $R^1$ and $R^2$ are not both acyl, if n is greater than 0 then $R^3$ is H, $R^4$ is H or methyl, $R^5$ is H or $C_1$-$C_{10}$ alkyl (e.g., methyl), X is $C_1$-$C_{12}$ alkyl or $C_1$-$C_{12}$ alkenyl.

A compound of formula I may be attached to any OH group of the compound of formula II to form the product (compound of Formula III); it is expected that the primary hydroxy groups would react preferentially. Examples of the products resulting from the reaction of a compound of formula I with a compound of formula II include the following compounds of Formula III:

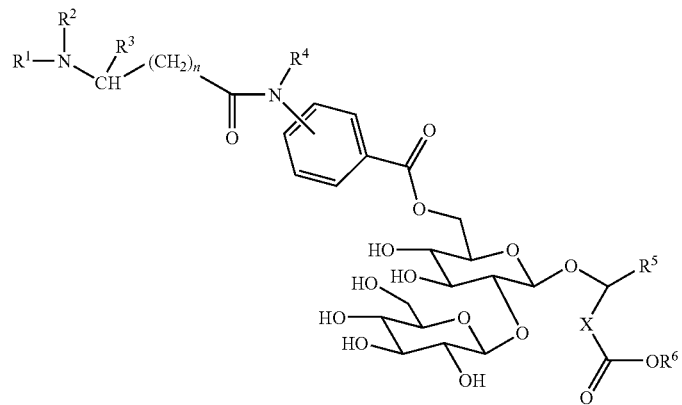
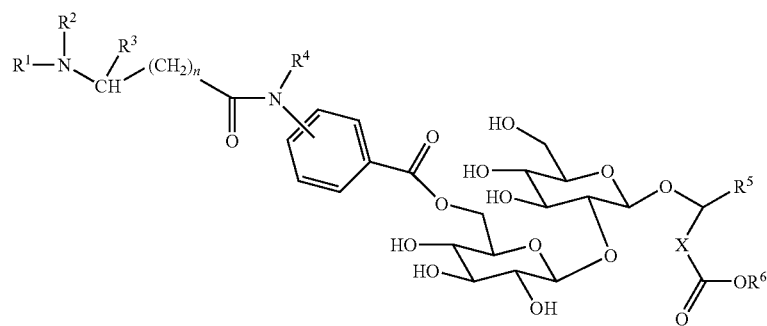
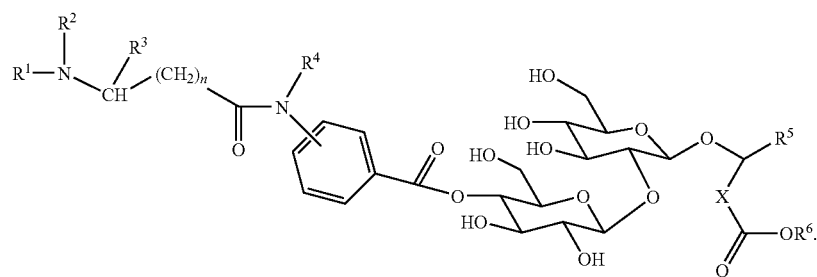
Preferred compounds of formula I are
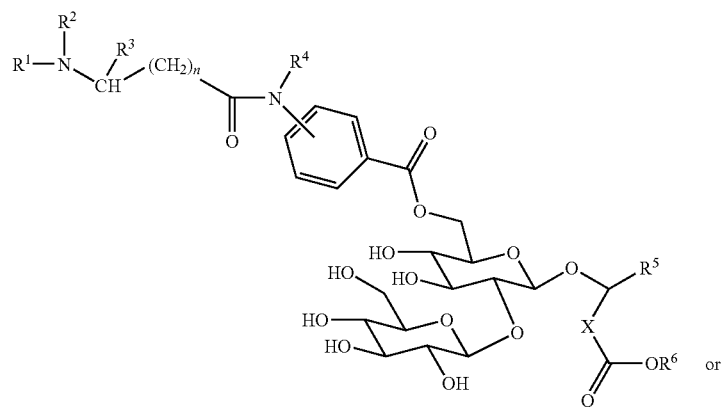

-continued

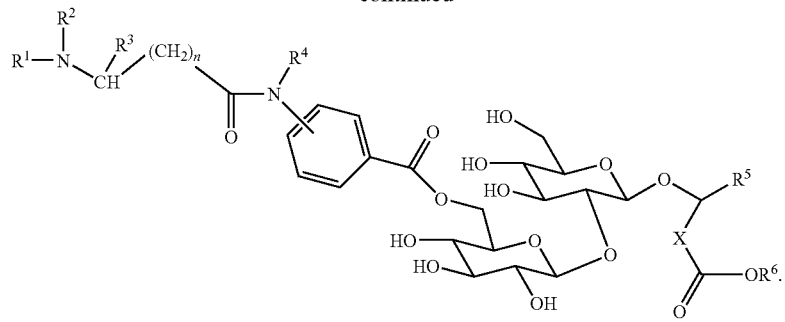

To form a compound of Formula II: Generally, crude sophorolipids (1.0 g), produced by methods known in the art (e.g., Solaiman, D. K. Y., et al., Biotech. Lett., 26: 1241-1245 (2004)), were reacted with base (e.g., potassium hydroxide, 0.3 g) in ethanol (e.g., 50 mL) at about room temperature for about 18 hours to give two products after workup: SL-ethyl ester ($R^6$=$CH_2CH_3$) and SL-free acid ($R^6$=OH). To produce SL-benzyl ester (R=benzyl), the SL-free acid was reacted with benzyl alcohol in the presence of condensation reagents (e.g., 1-[3-(dimethylamino)propyl]-3-ethylcarbodiimide hydrochloride and 4-dimethylaminopyridine) at about room temperature for about 18 hours.

To form a compound of Formula I: A compound of Formula I was easily made, for example, by reacting commercially available amino acids (e.g., N-benzyloxycarbonyl alanine, N-t-butyloxycarbonyl-4-hydroxyproline, N-t-butyloxycarbonyl glutamic acid α-t-butyl ester, N-ε-benzyloxycarbonyl lysine, and glutamic acid χ-benzyl ester) with carboxylic acids (e.g., propionic acid, palmitic acid), in the presence of amide-forming reagents (e.g., 1-[3-(dimethylamino)propyl]-3-ethylcarbodiimide hydrochloride, hydroxybenzotriazole, 4-dimethylaminopyridine), to give acylated amino acids (specific examples are given below). These compounds were reacted with p-aminobenzoic acid (paba)(or o-aminobenzoic acid or m-aminobenzoic acid), again in the presence of condensation reagents (e.g., 1-[3-(dimethylamino)propyl]-3-ethylcarbodiimide hydrochloride, hydroxybenzotriazole, 4-dimethylaminopyridine), to give acylated amino acid-paba derivatives (specific examples are given below). Alternatively, for example, commercial amino acids without any changes may be reacted with paba, or o-aminobenzoic acid or m-aminobenzoic acid (in organic solvents such as acetonitrile and THF at room temperature for about 18 to about 24 hours) to give amino acid-paba or amino acid-o-aminobenzoic acid or amino acid-m-aminobenzoic acid.

The compound of Formula I may be ortho, meta, or para relative to the benzene component:

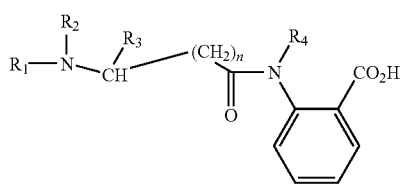

-continued

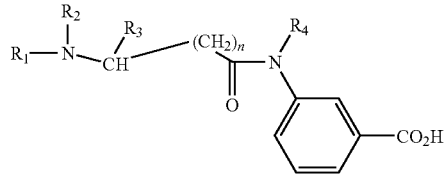

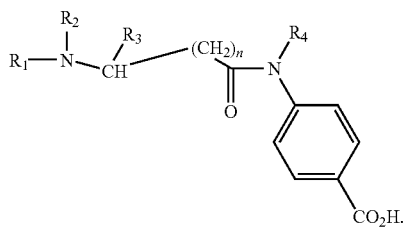

The preferred compounds of Formula I are

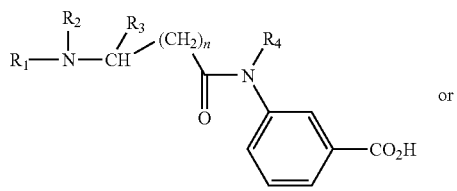

or

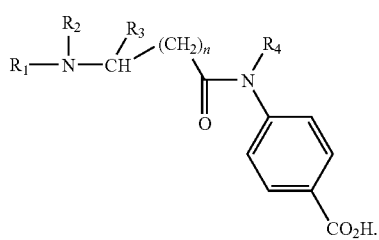

The most preferred compound of Formula I is

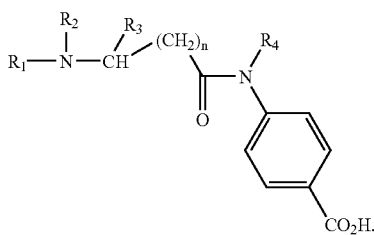

To form a compound of Formula III: The acylated amino acid-paba compounds (or amino acid-paba compounds; e.g., 1 mmol) and the SL-ester or SL-benzyl ester (e.g., 1.3-1.5 mmol) were dissolved in an organic solvent system (e.g., chloroform/dimethylformamide), the condensation reagents described above were added (e.g., 1.1 mmol each), and the mixture was heated to about 40° to about 60° C. (e.g., 40° to 60° C.; preferably about 50° to about 55° C. (e.g., 50° to 55° C.)) for about 1 to about 4 days (e.g., 1 to 4 days; preferably about 1 to about 2 days (e.g., 1 to 2 days), more preferably about 30 to about 40 h (e.g., 30 to 40 hours), most preferably about 36 h (e.g., 36 hours)) to give compounds of Formula III.

The compounds of Formula III may have surfactant properties in their own right. Generally, these acylated amino acid-paba-SL-esters (compounds of Formula III, approx. 1 mmol)) were treated with a deblocking reagent, either an acid such as trifluoroacetic acid (2 mL) for about 1 h at about room temperature, or hydrogen and a palladium catalyst (approx. 50-100 mg) in 50 mL of a solvent (e.g., tetrahydrofuran/ethanol) for about 2 to about 4 h at about room temperature, to reveal charged units in the resulting compounds of Formula IV. Formula IV is the same as Formula III except that one of the groups $R^1$ or $R^2$ of Formula III is replaced (by acidolytic or hydrogenolytic deprotection) with hydrogen.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

General: Protected amino acids (e.g., N-benzyloxycarbonyl alanine, N-t-butyloxycarbonyl-4-hydroxyproline, N-t-butyloxycarbonyl glutamic acid α-t-butyl ester, N-ε-benzyloxycarbonyl lysine, and glutamic acid χ-benzyl ester) were obtained commercially from Advanced Chemtech and Novabiochem. All solvents and reagents were used as received. Silica gel used for column chromatography was obtained from Fisher. NMR spectra were recorded on a Varian Associates Gemini 200 MHz instrument, and LCMS data were recorded on a Waters/Micromass ZMD instrument with ES or APC ionization.

Sophorolipids: SLs were prepared as previously reported, using stearic acid and glucose as carbon sources (Solaiman, D. K. Y., et al., Biotech. Lett., 26: 1241-1245 (2004)). The initial growth medium, containing 200 g glucose, 20 g yeast extract, and 2 g urea in 2 L deionized water, was prepared and autoclaved in a Bioflow III fermentation vessel. Before inoculation, the medium was supplemented with 45 g stearic acid. Frozen *C. bombicola* ATCC 22214 (NRRL Y-30816) inoculum (50 mL) was allowed to thaw and was then added to the medium. Fermentation was carried out at 26° C., 700 rpm, and an air flow of 2 L/min. No pH control was applied. At the 24-hr point of fermentation, filter-sterilized growth medium (prepared from 50 g glucose, 5 g yeast extract, and 0.5 g urea in 500 mL deionized water) and 100 g UV-sterilized glucose were added to the culture. At the 48-hr point, 50 g glucose and 45 g stearic acid, both UV-sterilized, were added. At the 96-hr point, another 45 g UV-sterilized stearic acid was added. Harvest was performed at 7 d by transferring the culture to centrifuge jars and centrifuging at 9000 rpm for 30 min. Supernatants were decanted from cell pellets and discarded. Cell pellets were lyophilized, then extracted with ethyl acetate by shaking at 250 rpm and 30° C. for 72 h. This mixture was filtered, and the solids washed with ethyl acetate. Solvent was removed from the combined organic solution on the rotary evaporator. The solid thus obtained was washed with 10:1 hexane/petroleum ether, then dried in a vacuum desiccator.

SL ethyl and benzyl esters: The crude SL (2 g) obtained from *C. bombicola* ATCC 22214 (NRRL Y-30816) fermentation above was added to a solution of KOH in ethanol and stirred at room temperature overnight. Complete solution was not obtained, but the mixture remained a pale yellow suspension. The reaction was acidified to an apparent pH of 4 with 2M HCl, and ethanol was removed on a rotary evaporator. The solid was washed with 2×10 mL water to remove acetic acid (produced from hydrolysis of acetyl groups on the crude SL), air dried, and purified by column chromatography on silica gel with 80/20/1 chloroform/methanol/water (referred to hereafter as solution A). Two products were obtained: SL ethyl ester (1.3 g) and SL free acid (0.4 g). The free acid (0.4 g, 0.64 mmol) was dissolved in 10 mL 3:1 chloroform/DMF (dimethylformamide). To this solution was added benzyl alcohol (2 mL, 19.3 mmol), 1-hydroxybenzotriazole hydrate (HOBt, 122 mg, 0.8 mmol), and 1-[3-(dimethylamino)propyl]-3-ethylcarbodiimide hydrochloride (EDC, 153 mg, 0.8 mmol). The mixture was stirred magnetically under $N_2$ for 36 h. DMF and $CHCl_3$ were removed using a rotary evaporator, and the material was purified with column chromatography on silica gel: first in 5% methanol/chloroform to remove benzyl alcohol, then with solution A to afford SL benzyl ester (373 mg, 82%). $^1H$ NMR ($d_6$-DMSO+$D_2O$): 1.11 d (3H), 1.20 br s (26H), 1.51 m (2H), 2.32 t (2H), 2.92-3.28, m (7H), 3.30-3.50 m (3H), 3.55-3.73 m (3H), 4.30 d (1H), 4.41 d (1H), 5.05 s (2H), 7.34 br s (5H).

Six examples of a compound of Formula I were reacted with a compound of Formula II (as produced above):

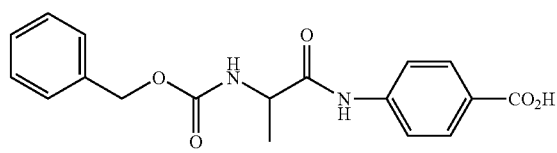

Ia

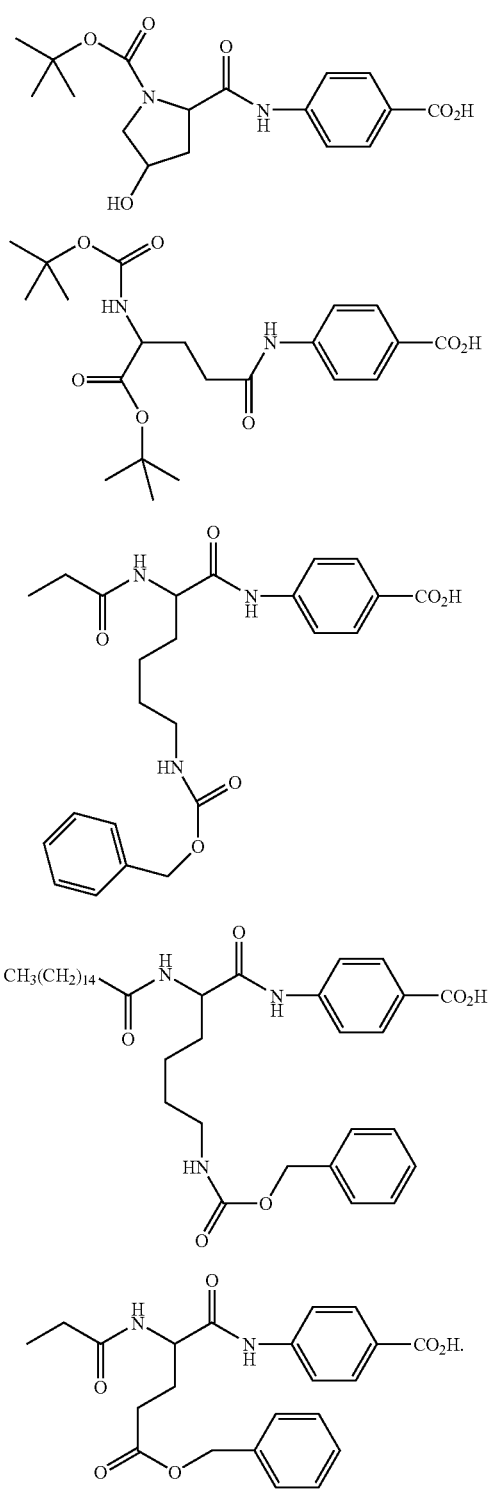

The resulting products were named, for example, IIIa, IIIb, etc. Products which subsequently underwent acidolytic or hydrogenolytic deprotection were named, for example, IVa, IVb, etc.

Synthesis of amino acid-derivatized sophorolipids: A representative procedure was as follows: A solution of propionic anhydride was prepared in situ by reacting propionic acid (0.48 g, 6.5 mmol) with EDC (614 mg, 3.2 mmol) in acetonitrile for 15 min at room temperature. This solution was then added over the course of 5 min to a magnetically stirred solution of N-ε-benzyloxycarbonyl lysine (Lys(Cbz)) (1 g, 3.6 mmol) in 36 mL 0.1 M NaOH and 20 mL 2-propanol. A fine white precipitate formed, another 36 mL 0.1 M NaOH was added, and stirring was continued overnight. The reaction mixture was then concentrated in vacuo to remove the organic solvents and acidified to a pH of 2.5 with 1M HCl. During acidification, the white precipitate dissolved. The aqueous solution was extracted with chloroform and then ethyl acetate. These organic solvents were combined and concentrated on the rotary evaporator to yield a colorless oil which was used without purification in the next step.

The crude propionyl-Lys(Cbz) thus obtained was dissolved in 10 mL 1:1 THF (tetrahydrofuran)/acetonitrile), and to this solution was added HOBt (460 mg, 3 mmol) and EDC (573 mg, 3 mmol). The solution was swirled at room temperature for 15 min, and then added over the course of 5 min to a solution of 4-aminobenzoic acid (Paba, 550 mg, 4 mmol) in 20 mL THF/acetonitrile. After addition, the reaction mixture was stirred overnight. Solvent was removed with rotary evaporation to yield a yellow semi-solid which was then stirred with 50 mL 1 M HCl. The liquid was decanted and the residue purified by column chromatography on silica gel with solution A. The product had an $R_f$ of 0.5 in this solvent system (510 mg, 35% based on initial use of propionic acid).

The propionyl-Lys(Cbz)-Paba (455 mg, 1 mmol) was dissolved along with SL-ethyl ester (900 mg, 1.38 mmol) in 6 mL 3:1 chloroform/DMF. To this solution was added HOBt (168 mg, 1.1 mmol), EDC (210 mg, 1.1 mmol), and 1,8-diazabicyclo[5.4.0]undec-7-ene (DBU, 149 μL, 1 mmol). Preliminary results had indicated that a strong base enhanced the rate of this reaction. The reaction mixture was heated under nitrogen to 50°-55° C. and stirred magnetically for 36 h. It was then concentrated on the rotary evaporator and purified by column chromatography on silica gel with solution A to afford compound IIId (0.56 g, 51%). Yields for compounds IIIa-g ranged from 35% to 55%.

Preparation of compounds IVa-g: For the surfactants requiring acid deprotection (IIIb and IIIc, which after acid deprotection we called IVb and IVc), a weighed amount of the compound was treated with 2 mL trifluoroacetic acid for 1 hr, after which 2 mL $CH_2Cl_2$ was added and reaction continued for another hour. The solvents were then removed under a stream of $N_2$ and rotart evaporated twice out of acetonitrile, then dried on a vacuum line overnight. The deprotected compounds were then dissolved in buffer for use in surface tension measurements.

For the other surfactants (involving IIIa and IIId-g, which after hydrogenolytic deprotection we called IVa and IVd-g), which required hydrogenolytic deprotection, the compound was dissolved in 50 mL $N_2$-sparged 2:1 THF/ethanol and 5% Pd/C was added (the ratio of weight of catalyst to weight of compound 1 was approximately 1:2 in all cases). $N_2$ was passed through the flask for 10 min, followed by $H_2$ at the rate of about 1 bubble/second as monitored with an oil bubbler. Progress of the reaction was monitored by TLC in solution A; $H_2$ bubbling was continued until starting material was gone. Reaction times ranged from 2 to 4 h. $N_2$ was bubbled through, and the mixture filtered first through Celite® 545, then through two layers of Whatman #1 filter paper. Solvent was removed on the rotary evaporator and the solid dried on the vacuum line overnight. Weighed portions of the dried solid were dissolved in buffer for use in surface tension measurements.

Surface Tension Measurements: Measurements were performed with the Wilhelmy plate method on a DataPhysics Instruments DCAT-11 tensiometer at ambient temperature, 21°-22° C. To avoid any effects that might arise from a change in counterions, the buffer used was 10 mM acetate/borate/phosphate since this combination can be adjusted to a wide range of pH by addition of NaOH. The buffer used to dissolve compound IV was used as the blank into which was titrated the surfactant solution. Solutions were filtered through a 1.2 micron Nylon syringe filter prior to use.

Results and Discussion. Selection of Targets: The design of molecules IVa-g was a result of several considerations. First, we chose to use the saturated stearic derivative of SL rather than the oleic version. While it might be argued that the saturated chain would lead to more compact packing in a micelle core, hence a lower cmc, than would the kinked oleic version, we wanted to demonstrate the utility of benzyl protection schemes for functionality at the head group, so the possibility that hydrogenolysis would also lead to reduction of the oleic C—C double bond led us to avoid that complication by employing the stearic derivative. Second was the choice of the carboxyl ester at the distal end of the lipid chain. There was no strong reason to prefer the ethyl ester; it was easy to prepare and work with, but other small alkyl esters would presumably also be. It does afford a convenient pattern in NMR spectra. We note that the preparation of this ethyl ester was accomplished by use of KOH in ethanol as the means for opening the macrolactone.

Finally, there is the choice of head group modifications themselves. We utilized a benzoate moiety (para-aminobenzoic acid, Paba) to link polyfunctional amino acids to the carbohydrate for two reasons: first, we have observed that the acetyl groups of the naturally occurring SL mixture were easily removed in protic solvents when only small amounts of base were present. Similarly, a simple acyl group such as glycine protected with a t-butoxycarbonyl (Boc) group was cleaved off SL to the extent of about 25% overnight in methanol with 1 equivalent of triethylamine, according to semi-quantitative HPLC data. The benzoate linker surprisingly appeared to negate this problem; we have never observed any decomposition of compounds III or IV under similar conditions. A further advantage was that benzoates were less susceptible to migration between carbohydrate hydroxyl groups. The benzoate unit also allowed for further derivatization. Second, and more importantly, without being bound by theory we believe that steric hindrance of any α-substituted amino acid will significantly inhibit acylation at the carbohydrate hydroxy groups. Preliminary results (data not shown) indicated that acylating the sophorose unit of SL with benzyloxycarbonyl (Cbz) protected alanine under the same conditions used for the amino acid-Paba units proceeded in yields around 10% after 72 h, while Boc-Leucine gave no product even when 4-dimethylaminopyridine (DMAP) was present as catalyst.

The amino acids we chose for this study were intended to provide a range of polar groups. Molecules IVa, IVb, IVd, and IVe were all cationic but with slight structural differences. The alanine and hydroxyproline derivatives IVa and IVb differ in that the latter had the added polar hydroxy group. The lysine derivative IVd had the charge extended away from the head group. The palmitoyl lysine derivative IVe had the added feature of a second hydrophobic chain. We believe this molecule fits the definition of a gemini surfactant (Chevalier, Y., Curr. Opinion Coll. & Interface Science, 7: 3-11 (2002)): the palmitoyl lysine unit represents one surfactant, the sophorolipid a second surfactant, and the spacer unit connecting the two is the Paba moiety. An anionic variant was provided by the propionyl glutamic acid derivative IVf, while the unsubstituted glutamic derivative IVc afforded a zwitterion. Finally, a different zwitterionic arrangement was provided by removal of the Cbz and benzyl groups of IIIg, giving the bolaform amphiphile IVg.

Synthesis: The preparation of products where the compound of Formula I was Ia-g relied upon carbodiimide-mediated coupling reactions, both for amide and ester formation, in conjunction with Boc, Cbz, t-butyl, and benzyl protection schemes. The SL benzyl ester used to prepare IIIg was obtained by reacting SL free acid with benzyl alcohol with EDC and HOBt. Derivatized amino acids (e.g. the propionyl and palmitoyl Lys and Glu) were prepared from symmetrical anhydrides. Linkage to the Paba spacer was accomplished similarly.

The more difficult step was attaching the compound amino acid-Paba units to the sophorose head group. There are seven hydroxy groups on SL, and in principle all of them could react with the benzoate, although the primary 6' and 6" hydroxy groups should react preferentially. An excess of SL ester was used to avoid formation of double-acylation products. When DMAP was added as a catalyst, no selectivity was observed: seven isomeric compounds of IIIa were observed by LCMS. The conditions reported above were those that gave the fewest number of isomers, two roughly equal in intensity and one minor one having 10-20% of the intensity of the two major peaks. Without being bound by theory, the two major isomers were the 6' and 6" adducts; at the very least, we feel confident that these two major isomers had the amino acid-Paba unit on different glucose rings, based on mass spec data (FIG. 1). Only one isomer showed a strong peak at M-163, corresponding to loss of glucose ($C_6H_{11}O_5$); this fragmentation should only occur for the isomer with the amino acid-Paba unit attached to the "internal" glucose ring, i.e. at the 6' position. The other major isomer did not show a M-163 peak.

Deprotection of molecules (where the compound of Formula III was IIIb and IIIc) with trifluoroacetic acid caused no damage to the glycoside linkage (i.e., cleavage of the ethyl 17-hydroxystearate was not observed). Compounds IVa-g had good solubility in water. Molecules IVb and IVd, for example, were readily soluble at 500 mg/100 mL at room temperature (higher concentrations should be achievable but were not tested due to limitations of material). By contrast, the ethyl ester of the oleic variant of SL was, in our hands, soluble only at about 8 mg/100 mL at room temperature.

Figure 2:
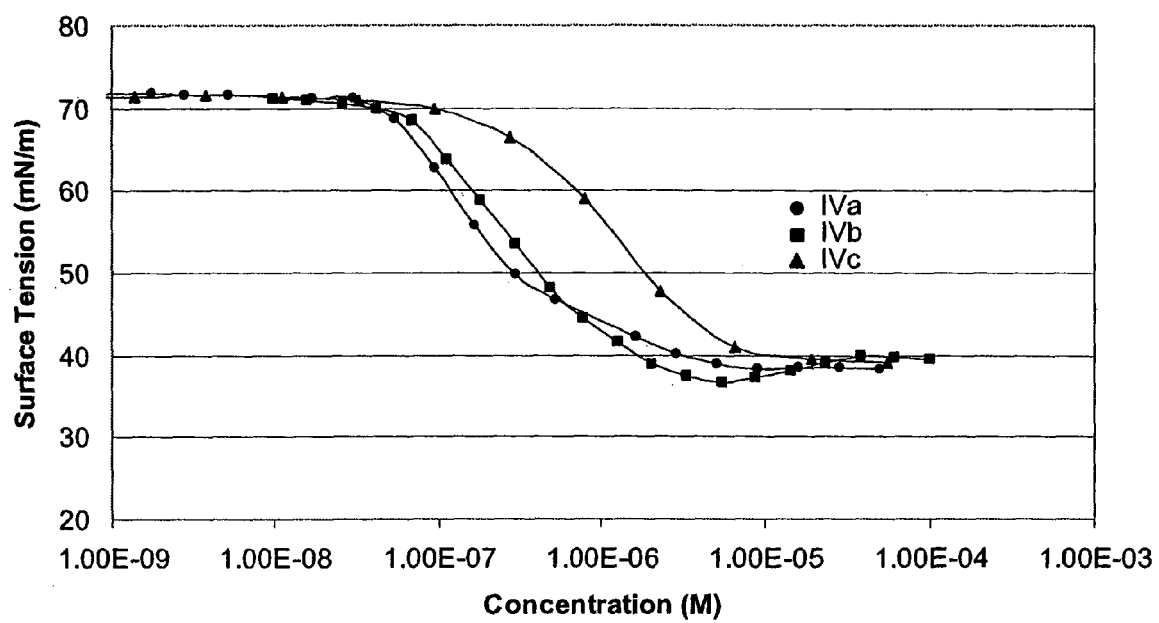
FIG. 2 shows representative surfactant behavior (concentration vs. surface tension) for several compounds (described below). All solutions were buffered at 10 mM and pH 5.8 with temperature=21°-22° C.

Surface Tension Measurements: FIG. 2 and Table 1 show that compounds IVa-g behave as surfactants. The cmc and $\chi_{min}$ values for the zwitterionic IVc appeared to vary little with pH, and even remained roughly the same in unbuffered solution. This latter feature was gratifying since it suggested that any specific ion effects due to the presence of a trifluoroacetate anion from the deprotection of a Boc-amino acid were probably negligible or at the very least can readily be counteracted in 10 mM buffer. The bolaform amphiphile IVg was not expected to form a classical micelle. It should, however, be able to assemble in a head-to-tail fashion into a vesicle. Without being bound by theory, this difference in self-assembly may be responsible for the higher cmc value observed for this molecule.

To what extent did the composition of compounds IVa-g as mixtures of isomers affect the cmc values of these materials? Without being bound by theory, differences in surfactant behavior of the 6' and 6" adducts for each compound may be minimal, especially after noting that all the charged SL variants prepared in this work had cmc values and $\chi_{min}$ values that differed little from each other. While it is true that the shape of the molecule at the hydrophilic head group was different for these two major isomers—the former had a branched shape, while the latter was more linear—and as a result aggregation in a micelle or vesicle would be expected to differ, we propose that the dynamic nature of these aggregates, the extensive hydrogen bonding that should occur for such carbohydrate surfactants in all isomers, the consistent shape of the hydrophobic portion, and the possibilities for rotamers at the glucose-glucose bond all contributed to minimize orientation or electrostatic effects associated with the different isomers. For example, although structurally the comparison was far from precise, the α and β anomers of several ethyl acylglucopyranosides differed by under a factor of 2 in cmc and by 2 or 3 mN/m in $\chi_{min}$ variations which may well lie within experimental error.

All of the references cited herein are incorporated by reference in their entirety. Also incorporated by reference in their entirety are the following references: Bisht, K. S., et al., J. Org. Chem., 64: 780-789 (1999); Bisht, K. S., et al., Macromolecules, 33: 6208-6210 (2000); Carr, J. A., and K. S. Bisht, Tetrahedron, 59: 7713-7724 (2003); Lang, S., et al., Chimica Oggi, 18: 76-79 (2000); Singh, S. K., et al., J. Org. Chem., 68: 5466-5477 (2003); Zhang, L., et al., Coll. Surf. A: Physicochem. Eng. Aspects, 240: 75-82 (2004).

Thus, in view of the above, the present invention concerns (in part) the following:

A sophorolipid wherein said sophorolid is produced by a method comprising (or consisting essentially of or consisting of) reacting a compound of formula I

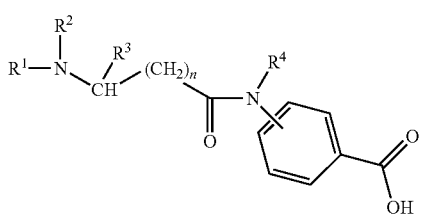

with a compound of formula II

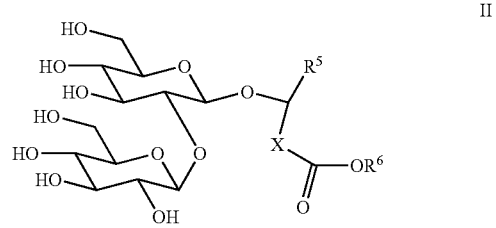

and at least one condensation reagent (e.g., 1-[3-(dimethylamino)propyl]-3-ethylcarbodiimide hydrochloride, hydroxybenzotriazole, 4-dimethylaminopyridine), wherein
$R^1$ and $R^2$ are H, $C_1$-$C_{18}$ alkyl, $C_3$-$C_{18}$ alkenyl, $C_3$-$C_{10}$ cycloalkyl, phenyl, or $C_1$ through $C_{18}$ acyl or alkoxycarbonyl,
$R^1$ and $R^2$ are not both acyl,
$R^3$ is H, $CH_3$, $CH_2$-phenyl, $CH_2$—$C_6H_4$—OH, $CH_2CO_2H$, $CH_2CH_2CO_2H$, $CH(CH_3)_2$, $CH_2CH(CH_3)_2$, $CH(CH_3)$ $CH_2CH_3$, $CH_2OH$, $CH(CH_3)OH$, $CH_2CH_2CH_2CH_2NH_2$, $CH_2CH_2CONH_2$, $CH_2CONH_2$, $CH_2$—$C_3N_2H_3$(histidine), $CH_2CH_2CH_2NHC(NH)NH_2$, $CH_2CH_2SCH_3$,
$R^2$ and $R^3$ may be joined in a ring,
$R^4$ is H, $C_1$-$C_{18}$ alkyl, $C_3$-$C_{18}$ alkenyl, $C_3$-$C_{10}$ cycloalkyl, or phenyl,
n is 0-6,
$R^5$ and $R^6$ are H, $C_1$-$C_{18}$ alkyl, $C_3$-$C_{18}$ alkenyl, $C_3$-$C_{10}$ cycloalkyl, or phenyl, and
X is $C_1$-$C_{18}$ alkyl or $C_1$-$C_{18}$ alkenyl;
optionally followed by acidolytic or hydrogenolytic deprotection which removes one of the groups $R^1$ or $R^2$ and replaces it with hydrogen.

The above sophrolipid, wherein the method further comprises acidolytic or hydrogenolytic deprotection wherein one of the groups $R^1$ or $R^2$ is replaced with hydrogen.

The above sophorolipid, wherein
$R^1$ and $R^2$ are H, methyl, or $C_1$ through $C_{18}$ acyl or alkoxycarbonyl,
$R^1$ and $R^2$ are not both acyl,
if n is greater than 0 then $R^3$ is H,
$R^4$ is H or methyl,
$R^5$ is H or $C_1$-$C_{10}$ alkyl (e.g., methyl),
X is $C_1$-$C_{12}$ alkyl or $C_1$-$C_{12}$ alkenyl.

The above sophorolipid, where said compound of formula I is not

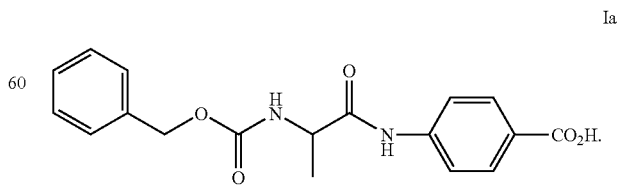

The above sophorolipid, wherein said sophorolipid is selected from the group consisting of

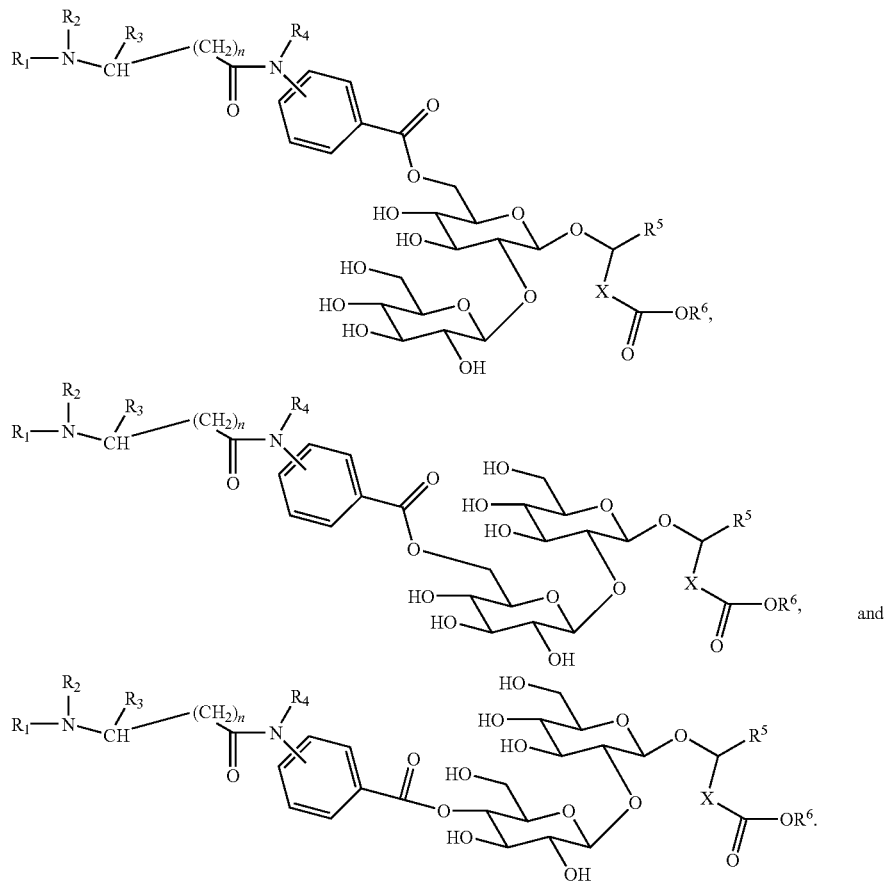

A sophorolipid (glycolipid) containing composition, said composition comprising (or consisting essentially of or consisting of) a carrier and at least one sophorolipid described above.

The above sophrolipid containing composition, wherein the carrier is water or an alcohol.

The above sophorolipid containing composition, where said compound of formula I is not

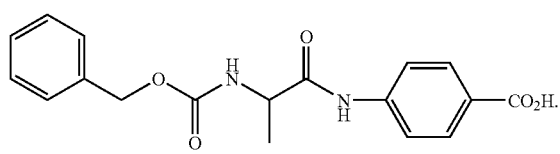

Ia

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Tensiometry Data for Compounds IVa-g[a]

| Compound | cmc (µM) | $\Gamma_{min}$ |
|---|---|---|
| IVa, pH = 5.8 | 8 | 38.5 |
| IVb, pH = 5.8 | 5.7 | 37 |
| IVb, pH = 9.1 | 24 | 42 |
| IVc, unbuffered | 13 | 40 |
| IVc, pH = 2.5 | 17 | 40.8 |
| IVc, pH = 5.8 | 14 | 38.7 |
| IVc, pH = 9.1 | 17 | 40.2 |
| IVd, pH = 5.8 | 15 | 38.8 |
| IVe, pH = 5.8 | 6 | 47 |
| IVf, pH = 2.5 | 110 | 48.5 |
| IVf, pH = 5.8 | 51 | 43.0 |
| IVg, pH = 5.8 | 85 | 39.5 |

[a]Measurements were performed in duplicate

We claim:

1. A sophorolipid produced by a method comprising reacting a compound of formula I

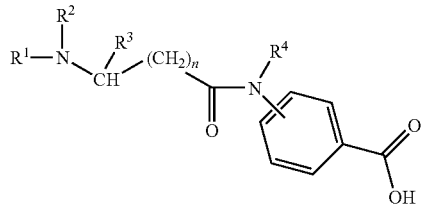

with a compound of formula II

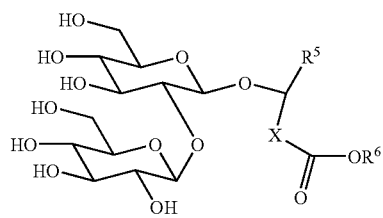

wherein

R[1] and R[2] are H, $C_1$-$C_{18}$ alkyl, $C_3$-$C_{18}$ alkenyl, $C_3$-$C_{10}$ cycloalkyl, phenyl, or $C_1$ through $C_{18}$ acyl or $C_1$ through $C_{18}$ alkoxycarbonyl, R[1] and R[2] are not both acyl, R[3] is H, $CH_3$, $CH_2$-phenyl, $CH_2$—$C_6H_4$—OH, $CH_2CO_2H$, $CH_2CH_2CO_2H$, $CH(CH_3)_2$, $CH_2CH(CH_3)_2$, $CH(CH_3)CH_2CH_3$, $CH_2OH$, $CH(CH_3)OH$, $CH_2CH_2CH_2CH_2NH_2$, $CH_2CH_2CONH_2$, $CH_2CONH_2$, $CH_2$—$C_3N_2H_3$(histidine), $CH_2CH_2CH_2NHC(NH)NH_2$, $CH_2CH_2SCH_3$, $CH_2CH_2CO_2CH_2C_6H_5$, $CH_2CH_2CH_2CH_2NHCOOCH_2C_6H_5$, or $COOC_4H_9$, R[2] and R[3] may be joined in a ring, R[4] is H, $C_1$-$C_{18}$ alkyl, $C_3$-$C_{18}$ alkenyl, $C_3$-$C_{10}$ cycloalkyl, or phenyl, n is 0-6, R[5] and R[6] are H, $C_1$-$C_{18}$ alkyl, $C_3$-$C_{18}$ alkenyl, $C_3$-$C_{10}$ cycloalkyl, or phenyl, and X is $C_1$-$C_{18}$ alkyl or $C_1$-$C_{18}$ alkenyl;

optionally followed by acidolytic or hydrogenolytic deprotection wherein one of the groups R[1] or R[2] is replaced with hydrogen.

2. The sophrolipid according to claim 1, wherein said method further comprises acidolytic or hydrogenolytic deprotection wherein one of the groups R[1] or R[2] is replaced with hydrogen.

3. The sophorolipid according to claim 1, wherein

R[1] and R[2] are H, methyl, or $C_1$ through $C_{18}$ acyl or $C_1$ through $C_{18}$ alkoxycarbonyl, R[1] and R[2] are not both acyl, if n is greater than 0 then R[3] is H, R[4] is H or methyl, R[5] is H or $C_1$-$C_{10}$ alkyl, and X is $C_1$-$C_{12}$ alkyl or $C_1$-$C_{12}$ alkenyl.

4. The sophorolipid according to claim 1, wherein said compound of formula I is

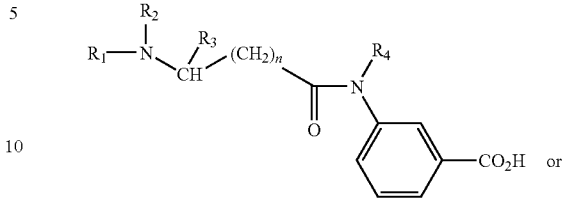

5. The sophorolipid according to claim 1, wherein said compound of formula I is

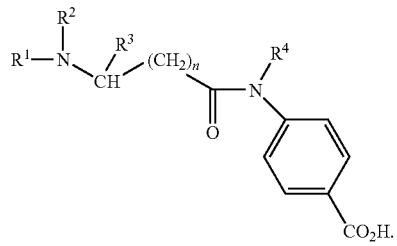

6. The sophorolipid according to claim 1, wherein said compound of formula I is selected from the group consisting of

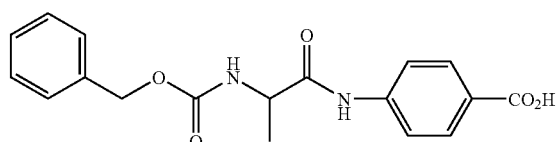

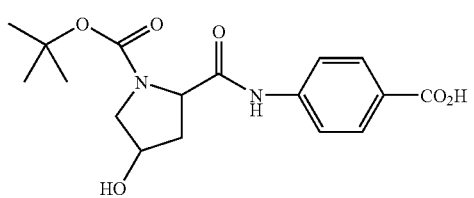

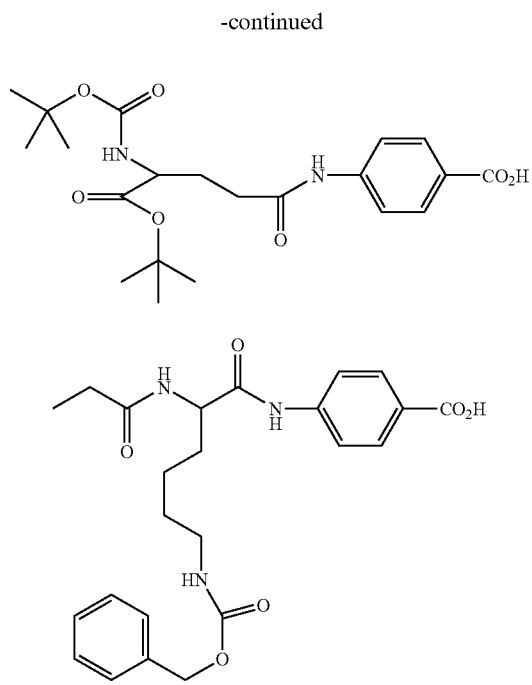
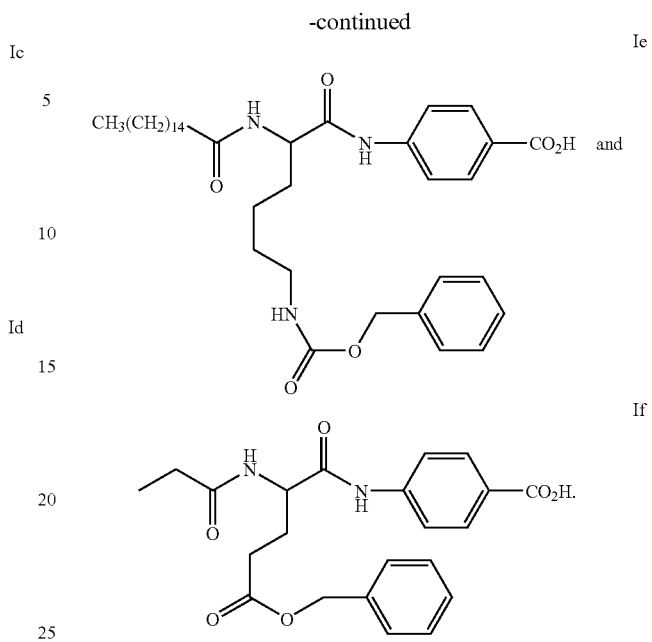
7. The sophorolipid according to claim 1, wherein said sophorolipid is selected from the group consisting of
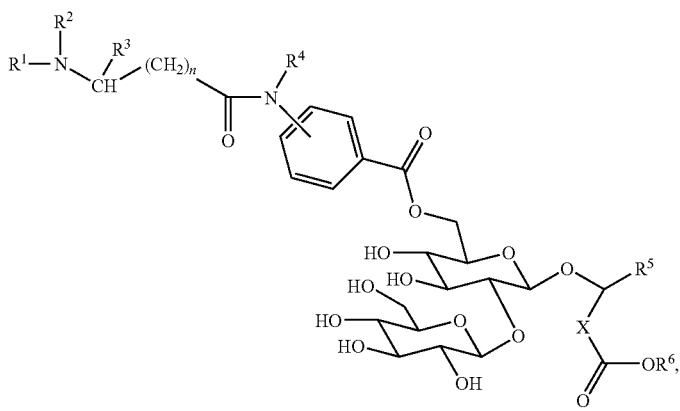
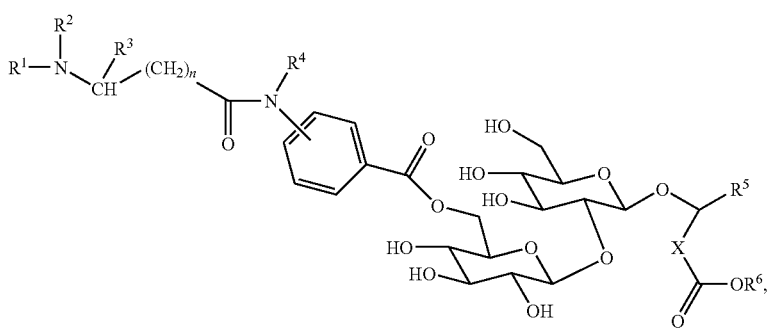

-continued

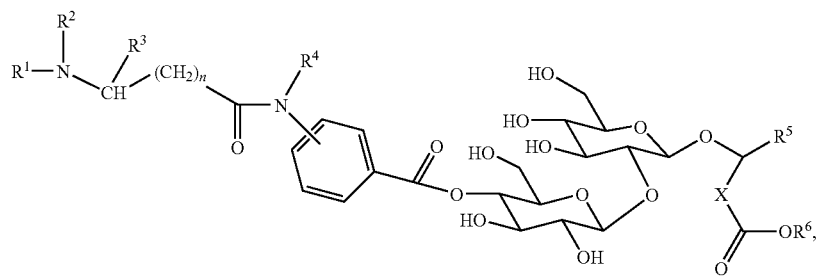

and mixtures thereof.

8. The sophorolipid according to claim 1, wherein said sophorolipid is

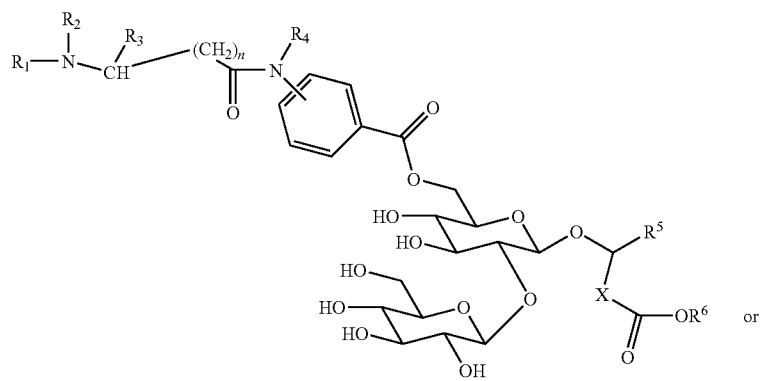

or

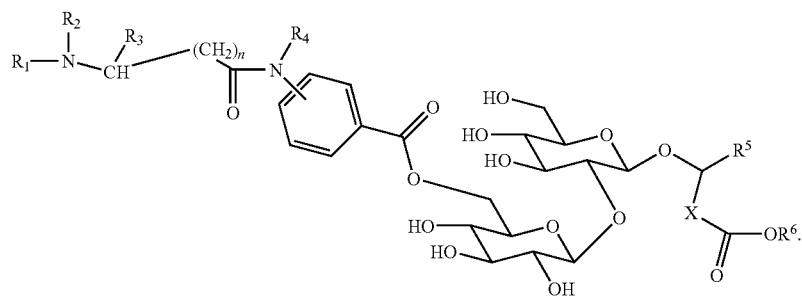

9. The sophorolipid according to claim 1, wherein said compound of formula I and said compound of formula II are dissolved in a solvent system with condensation reagents to form a mixture and said mixture is heated to about 40° to about 60° C. for about 1 to about 4 days to form said sophrolipid.

10. The sophorolipid according to claim 9, wherein said solvent system is chloroform/dimethylformamide.

11. The sophorolipid according to claim 9, wherein said condensation reagents are selected from the group consisting of 1-[3-(dimethylamino)propyl]-3-ethylcarbodiimide hydrochloride, hydroxybenzotriazole, 4-dimethylaminopyridine, and mixtures thereof.

12. The sophorolipid according to claim 1, said method further comprising acidolytic or hydrogenolytic deprotection wherein one of the groups $R^1$ or $R^2$ is replaced with hydrogen.

13. A sophorolipid containing composition, said composition comprising a carrier and at least one sophorolipid according to claim 1.

* * * * *